US012539408B1

(12) United States Patent
Basaran et al.

(10) Patent No.: US 12,539,408 B1
(45) Date of Patent: Feb. 3, 2026

(54) NEUTRAL DISPLACEMENT MEDICAL CONNECTOR

(71) Applicant: Asset Medical, Inc., San Diego, CA (US)

(72) Inventors: Ahmet Reha Basaran, Istanbul (TR); Mehmet Tüysüz, Mugla (TR)

(73) Assignee: Asset Medical, Inc., San Diego, CA (US)

( * ) Notice: Subject to any disclaimer, the term of this patent is extended or adjusted under 35 U.S.C. 154(b) by 0 days.

(21) Appl. No.: 19/018,277

(22) Filed: Jan. 13, 2025

(51) Int. Cl.
*A61M 39/10* (2006.01)

(52) U.S. Cl.
CPC ..... *A61M 39/10* (2013.01); *A61M 2039/1066* (2013.01); *A61M 2039/1072* (2013.01); *A61M 2205/0216* (2013.01)

(58) Field of Classification Search
CPC .......... A61M 39/10; A61M 2039/1066; A61M 2039/1072; A61M 2039/1027; A61M 2205/0216
See application file for complete search history.

(56) References Cited

U.S. PATENT DOCUMENTS 3,896,853 A 7/1975 Bernhard
5,695,466 A 12/1997 Lopez et al.
5,839,715 A * 11/1998 Leinsing ............. A61M 39/045 604/905
6,063,062 A 5/2000 Paradis
6,840,501 B2 1/2005 Doyle
6,994,315 B2 2/2006 Ryan et al.
7,722,575 B2 5/2010 Lopez
7,784,766 B2 8/2010 Guala
8,002,765 B2 8/2011 Lopez
8,048,038 B2 11/2011 Guala
8,096,525 B2 1/2012 Ryan
8,241,268 B2 8/2012 Whitley
8,758,306 B2 * 6/2014 Lopez ................... A61M 39/10 604/533
9,192,753 B2 11/2015 Lopez et al.
9,205,243 B2 12/2015 Lopez et al.
9,604,047 B2 3/2017 Newton et al.
9,750,926 B2 9/2017 Lopez et al.
10,195,413 B2 2/2019 Lopez
10,391,293 B2 8/2019 Fangrow
10,744,314 B2 8/2020 Siopes et al.
11,071,852 B2 7/2021 Lopez et al.
12,102,786 B2 10/2024 Fangrow
(Continued)

FOREIGN PATENT DOCUMENTS

CA 2581547 C 7/2010
EP 1529549 A1 5/2005
WO 2004084969 A2 10/2004

*Primary Examiner* — James D Ponton
(74) *Attorney, Agent, or Firm* — Carter, DeLuca & Farrell LLP; George Likourezos

(57) ABSTRACT

The disclosure proposes a medical connector including an elongated portion with a body portion and a proximal tip that is more proximal to the first end than the body portion. The body portion is tapered, such that a radial width of the body portion decreases towards the proximal tip. The elongated portion further includes one or more side openings on the body portion, and an internal fluid passageway in fluid communication with the one or more side openings. The one or more side openings are more distal than the abutment surface.

16 Claims, 5 Drawing Sheets

(56) References Cited

U.S. PATENT DOCUMENTS

| | | | | |
|---|---|---|---|---|
| 2003/0199835 | A1 | 10/2003 | Leinsing et al. | |
| 2004/0002684 | A1 | 1/2004 | Lopez | |
| 2005/0151105 | A1 | 7/2005 | Ryan et al. | |
| 2007/0007478 | A1 | 1/2007 | Leinsing et al. | |
| 2008/0103482 | A1 * | 5/2008 | Fangrow | A61M 39/22 604/523 |
| 2016/0129235 | A1 * | 5/2016 | Ryan | A61M 39/1011 604/535 |
| 2022/0184368 | A1 | 6/2022 | Lopez et al. | |

* cited by examiner

NEUTRAL DISPLACEMENT MEDICAL CONNECTOR

TECHNICAL FIELD

The disclosure relates to medical connectors for communication of medical fluids. In particular, the disclosure relates to neutral displacement medical connectors.

BACKGROUND

Neutral displacement medical connectors are used for communication of medical fluids to a patient. Such connectors generally include an elongated, axially extending spike having side openings close to a tip thereof. Around the spike, a flexible seal member can be provided, which is biased to a closed position. By distally pushing with a tip of a medical implement, the seal member can be brought into an open position in which the side openings are exposed to an inner space of the tip. U.S. Pat. No. 10,391,293 B2 discloses an example to such prior art connectors.

Most of the components of such connectors, especially spikes are made of delicate building materials. The spikes are geometrically prone to easily bend or rupture when subjected to non-axial (that is, radial or tangential) forces at extraction of the medical implements from the connectors. This shortens the service life and requires a great extent of attention in order to avoid such non-axial forces. The side openings further reduce the mechanical resistance of the spike, since there is inherently a decreased amount of building material in-between consecutive side openings.

Furthermore, it is intricate to accurately obtain the expected side opening geometries by molding; easily resulting in side openings that are smaller than their pre-determined designs. So, passing medical fluids through the side openings at a desired rate becomes a challenge, that can require an enormous extent of force due to increased pressure drop and drag forces around the side openings. In some cases, the molding process can even completely fail to form one or more of the side openings. So, it is difficult to obtain a connector that is in accordance with an original design.

Accordingly, it is desired to develop an improved medical connector.

SUMMARY

An aspect of the disclosure is to propose a medical connector that overcomes the shortcomings in the prior art.

A further aspect of the disclosure is to propose a medical connector with an enhanced ease of production and use. An even further aspect of the disclosure is to propose a medical connector with enhanced reliability. An even further aspect of the disclosure is to propose a medical connector with enhanced service life. An even further aspect of the disclosure is to propose a medical connector with enhanced overall clinical performance at least in terms of reduction of reflux, increased flow rate, and increased available flow rate to facilitate use.

These aspects are achieved by a set of features recited in the appended claims. Accordingly, the disclosure proposes a neutral displacement medical connector, in other words, neutral connector. The neutral connector is hereinafter referred to as "medical connector" or briefly "connector".

The connector extends along a main axis, thereby defining the main axis. Within the context of the disclosure, the main axis is parallel or coincident with an orientation along which a medical implement for being reversibly coupled with the connector can be translationally moved relative to the connector.

The connector comprises a body member having a proximal first end and a second end distal to the first end. The connector further comprises a base member that is coupled to the body member. An internal cavity is formed between the body member and the base member.

At the first end, the body member includes a central opening for receiving a male luer tip of a medical implement to transit a seal member from a closed position to an open position. In other words; at the first end, the body member defines the central opening for receiving the male luer tip of the medical implement to deliver fluid through the central opening.

The body member further includes an internal abutment surface located in-between the central opening and second end of the body member with regard to the orientation, that is, along the main axis. The abutment surface comprises a proximal end and a distal end. The abutment surface further comprises a slanting wall extending between the proximal end and the distal end; such that the proximal end of the abutment surface is radially narrower than the distal end of the abutment surface with respect to the main axis.

The connector further includes a rigid, hollow elongated portion located within the cavity. The elongated portion can be considered as an integral part of the base member, proximally extending towards the central opening.

The elongated portion includes a body portion and a proximal tip that is more proximal to the first end than the body portion. The body portion is tapered, such that a radial width of the body portion decreases towards the proximal tip. Within the context of the disclosure, the term "radial" refers to directions that are orthogonal to the main axis.

The elongated portion further includes one or more side openings on the body portion. The elongated portion further includes an internal fluid passageway in fluid communication with the one or more side openings. In other words, the elongated portion can be considered to define the one or more side openings and the internal fluid passageway.

The one or more side openings can includes a first end and a second end, wherein the first end of the one or more side openings is relatively closer to the central opening when compared to the second end. In other words, one or more side openings comprise a proximal first end and a distal second end.

When measured parallel to the main axis, a distance from the central opening to the distal end of the abutment surface is relatively shorter than a distance from the central opening to the first end of the side openings. In other words, the first end of the one or more side openings is more distal than the distal end of the abutment surface; in other words, the first end of the one or more side openings are positioned distally of the distal end of the abutment surface.

Considering that the one or more side openings are provided on the tapered body portion of the elongated portion; the relatively distal positioning of the one or more side openings with regard to the abutment surface results in that a greater portion of circumference around the main axis is available for being occupied by the one or more side openings. This minimizes geometric limitations in designing the one or more side openings in terms of circumferential width thereof. So, the disclosure renders possible to form relatively wider side opening(s) when compared to those in commercially available neutral displacement medical connectors. This provides an enhanced extent of flexibility in designing the one or more side openings. The mechanical resistance of the elongated portion against radial or tangential forces is not compromised by said design flexibility; so, the connector has an enhanced service life.

The flexibly designable one or more side openings allow transfer of medical liquids therethrough, without necessitating exertion of a high extent of pressure difference between radially inner and outer sides of the one or more side openings, at transferring medical liquids therethrough. So, the disclosure enables higher flow areas at the one or more side openings, for decreasing the necessary extent of said pressure difference between said radially inner and outer sides of the one or more side openings. Greater flow areas at the one or more side openings also result in greater accuracy in formation of the side openings by molding.

The disclosure allows complete functionality even with a single side opening that can be provided with a sufficient extent of flow area, without compromising the mechanical resistance of the elongated portion. Hence, a possible embodiment of the connector can comprise a single side opening.

In an aspect of the disclosure, the one or more side openings can have a pyriform geometry with a first end and second end, the first end being more pointy when compared to the second end. The relatively pointy first end of the pyriform geometry can correspond to first end(s) of respective one(s) of the side opening(s).

In another aspect of the disclosure, the one or more side openings can have a trapezoid geometry with a first base and a second base that is relatively longer than the first base, e.g., in a rotational direction around the main axis. The relatively shorter first base of the trapezoid geometry can correspond to the first end(s) of respective one or more side opening(s). The trapezoid geometry can be an isosceles trapezoid geometry.

In another aspect of the disclosure, an elastomeric seal member can be located within the internal cavity; the seal member can comprise a proximal end, a distal end and an interior region; the proximal end of the seal member can comprise a septum having a vertical thickness. The septum can be provided with a slit biased to the closed position; in other words, the septum can be arranged to define and the slit biased to the closed position. The seal member can further comprise an elastomeric collar located distal from the proximal end of the seal member but closer to the proximal end of the seal member than to the distal end of the seal member. A vertical thickness of the collar can be greater than the vertical thickness of the septum.

In another aspect of the disclosure, the seal member can be configured to move between the closed position and the open position in which the seal member is compressed when the male luer tip of the medical implement is inserted into the central opening. In other words, in the open position, the seal member is compressed axially away from the central opening. In other words, in the open position, the seal member is compressed in the distal direction.

In another aspect of the disclosure, the body portion can extend proximally from the base member, and the proximal tip of the elongated portion can be located further in the proximal direction than the proximal end of the abutment surface. In other words, in such aspect of the disclosure, the proximal tip of the elongated portion is located proximally of the proximal end of the abutment surface.

In another aspect of the disclosure, the elongated portion can include a closed, non-sharp (e.g., rounded), proximal tip for being received by the male luer tip when the seal member is in the open position.

In another aspect of the disclosure, the base member can be formed by molding.

In another aspect of the disclosure, the base member can include a male luer end.

In another aspect of the disclosure, the base member can include a flexible tube (that can be arranged for serving as, e.g., an inlet or an outlet); the flexibility of the tube provides suitability for facilitating engagement with medical implements that have different diameters. Such flexible tube thus can be considered as an adapter.

BRIEF DESCRIPTION OF THE DRAWINGS

Exemplary aspects according to the disclosure are hereinafter discussed in detail with reference to the following drawings. The drawings are provided for illustrative purposes only, and the intended scope of protection is not limited to the subject matter illustrated in the drawings.

REFERENCE SIGNS

Figure 1:
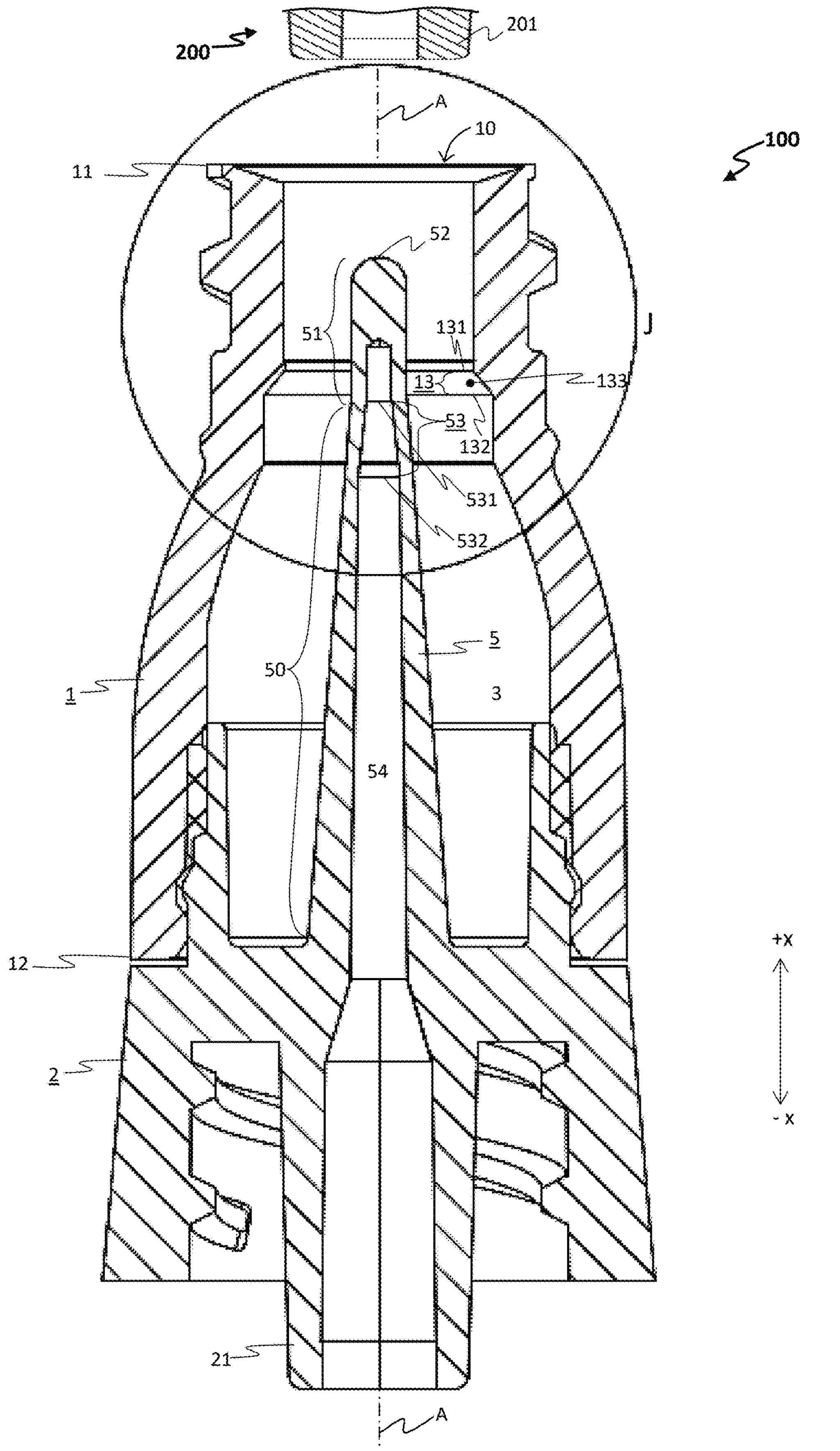
FIG. 1 shows an axial section view of a medical connector according to the disclosure, in which the seal member is extracted for enhanced clarity in visualization.
Figure 2:
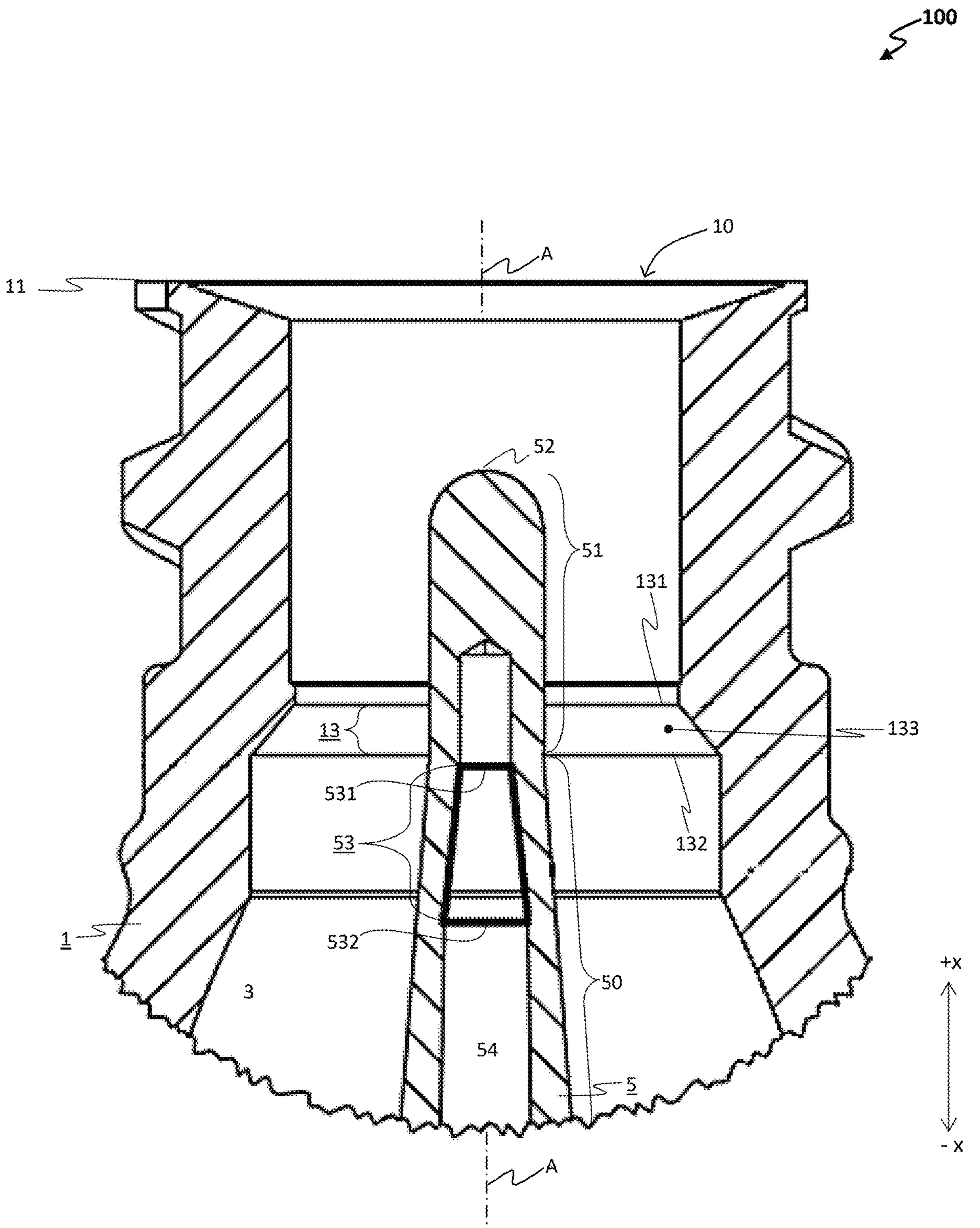
FIG. 2 is close-up view of detail J from FIG. 1, showing the alignment of an exemplary embodiment of a side opening relative to the abutment surface. In this embodiment, the side opening can be considered to have a trapezoid geometry within the context of the disclosure.
Figure 3:
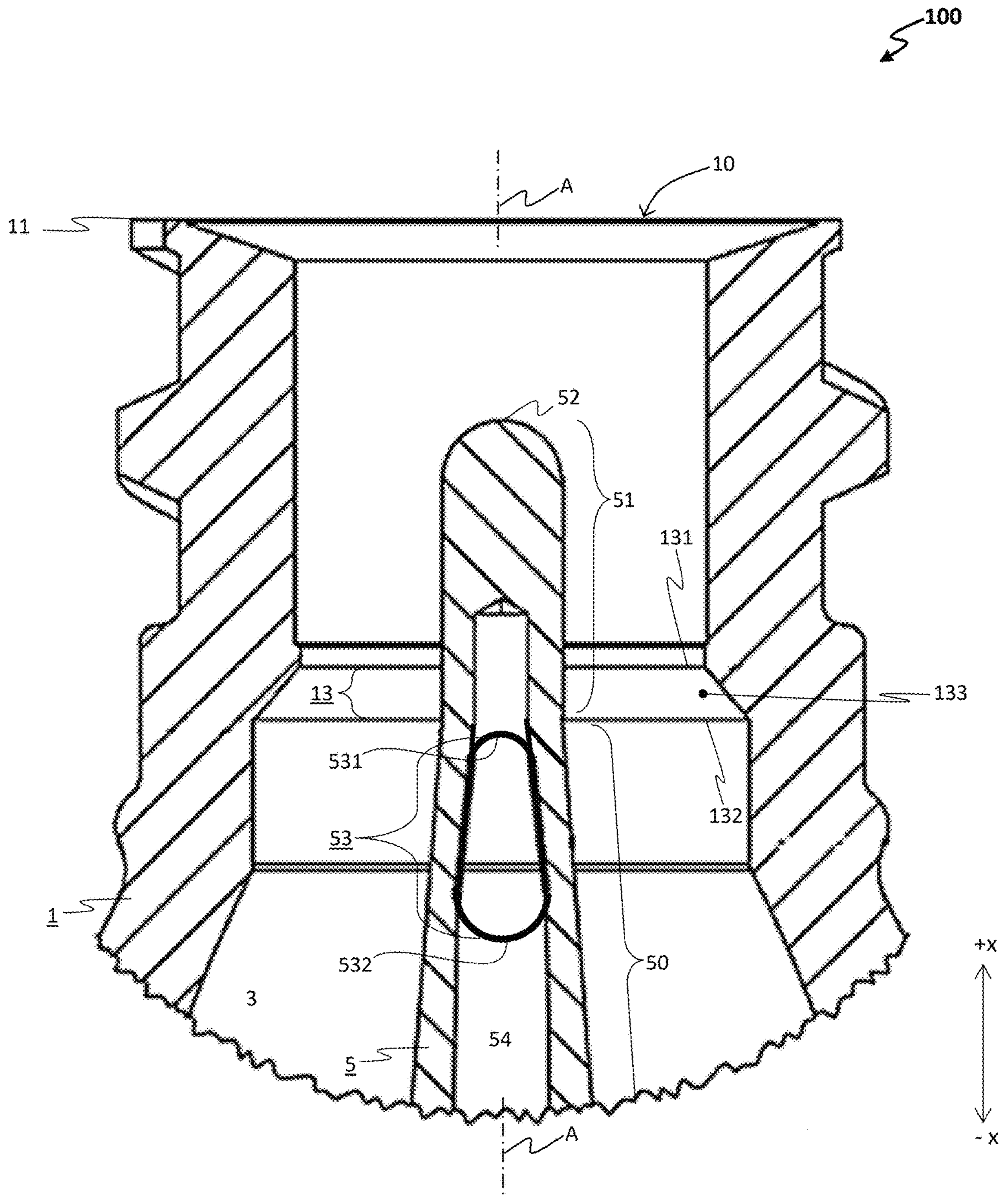
FIG. 3 is close-up view of a detail that is comparable with FIG. 2, showing the alignment of another exemplary embodiment of a side opening relative to the abutment surface. In this embodiment, the side opening can be considered to have a pyriform geometry within the context of the disclosure.
Figure 4:
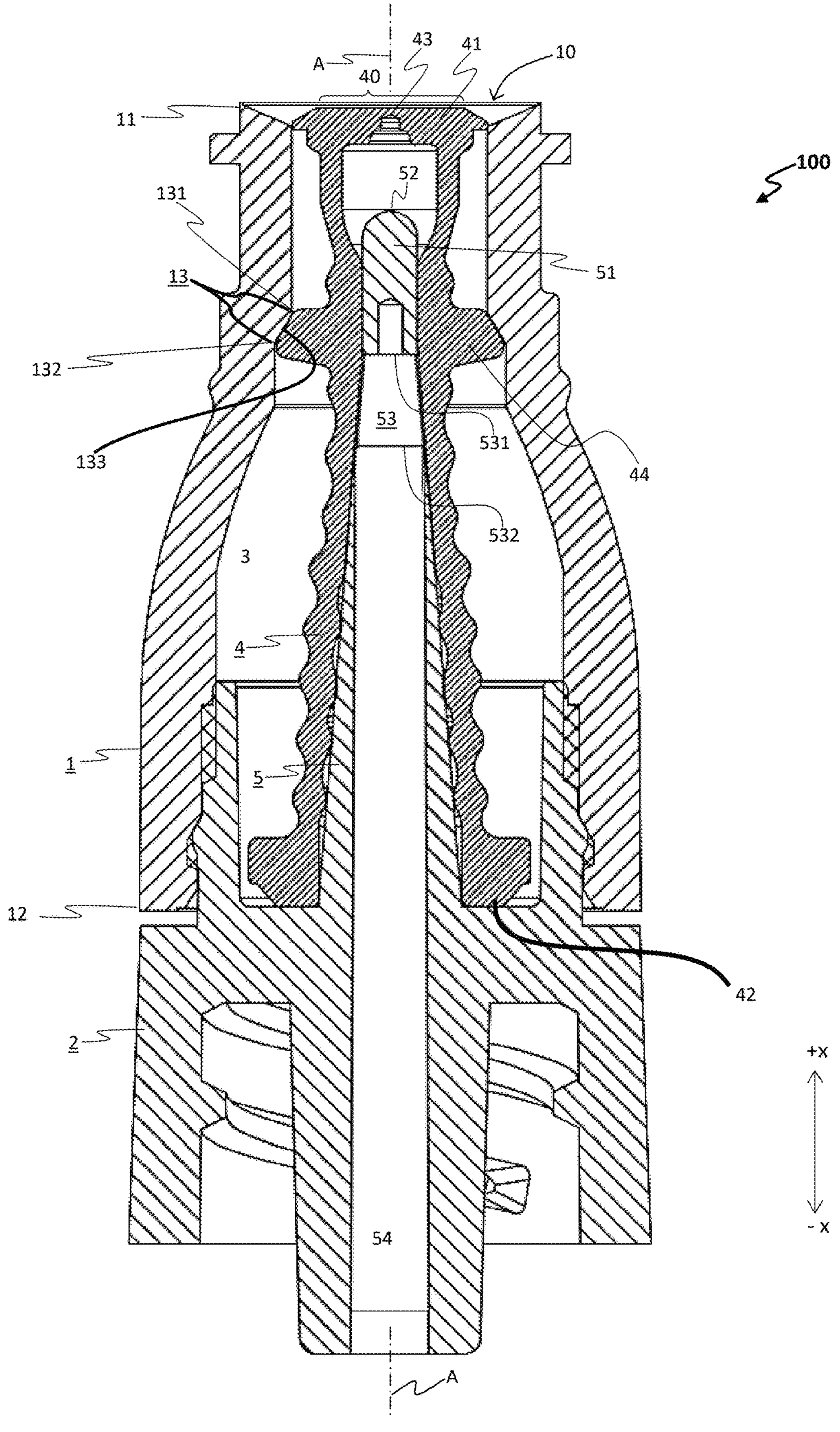
FIG. 4 shows an axial section view of a medical connector according to the disclosure, including an exemplary embodiment of the seal member.

1 proximal body member
10 central opening
11 first end (of the proximal body member (1))
12 second end (of the proximal body member (1))
13 abutment surface
131 proximal end (of the abutment surface (364))
132 distal end (of the abutment surface (364))
133 slanting wall
2 base member
21 male end
3 internal cavity
4 seal member
40 septum
41 proximal end (of the seal member (4))
42 distal end (of the seal member (4))
43 slit
44 collar
5 elongated portion
50 body portion
51 tip
52 top surface
53 side opening
54 passageway
531 first end (of the side opening (53))

532 second end (of the side opening (53))
100 connector
200 implement
201 male luer tip
A main axis
+X proximal direction
−x distal direction
+x/−x orientation Detailed Description of the Embodiments With reference to the appended drawings, the disclosure proposes a medical connector (100) including a body member (1) and a base member (2). The body member (1) is coupled to the base member (2). The body member (1) and base member (2) can be considered to form a housing.

It can be considered that the medical connector (100) extends along an orientation (+x/−x) that is parallel or coincident with a main axis (A) of the connector (100). The orientation (+x/−x) can be defined over a proximal direction (+x) and a distal direction (−x) opposite to the proximal direction (+x). The orientation (+x/−x) can also be referred to as a vertical orientation. For instance, a vertical thickness of a feature refers to that such thickness is assumed to extend along the orientation (+x/−x) defined above.

Throughout the specification, in this sense, various features are characterized or referred to as "distal" or "proximal", in accordance with their comparative positionings with regard to one another, mutatis mutandis. For instance, the body member (1) is herein considered more proximal than the base member (2); and thus, the body member (1) can be also referred to as proximal body member (1).

For receiving a male luer tip (201) of a medical implement (200), the body member (1) includes a central opening (10), that can be also referred to as proximal opening and can be considered as located at a proximal first end (11) of the body member (1). Thus, the medical connector (100) is configured to be removably attached to a medical implement (200) having a male luer tip (201). It can be considered that the male luer tip (201) is introduced through the central opening (10) along the main axis (A). In other words, it can be considered that the male luer tip (201) can be approached, introduced and removably engaged to the connector (100) through the central opening (10), by moving the medical implement (200) relative to the body member (1) along the main axis (A) in the distal direction (−x). Disengagement of the male luer tip (201) is performed by pulling the medical implement (200) in the proximal direction (+x), that is, opposite to the distal direction (−x).

The body member (1) further includes a second end (12) distal to the first end (11). Within the sense discussed above, the second end (12) is to be considered and referred to as a distal end with regard to the orientation (+x/−x). The body member (1) further includes an internal abutment surface (13) located in-between the central opening (10) and second end (12) of the body member (1) with regard to the orientation (+x/−x). In other words, the abutment surface (13) is located distal from the central opening (10), but closer to the central opening (10) than to the second end (12) of the body member (1).

The abutment surface (13) includes a proximal end (131), a distal end (132), and a slanting wall (133) extending between the proximal end (131) and distal end (132); such that the proximal end (131) of the abutment surface (13) is narrower than the distal end (132) of the abutment surface (13).

The base member (2) can include a male end (21) that extends in the distal direction (−x).

An internal cavity (3) is formed between the body member (1) and the base member (2). It can be considered that an elastomeric seal member (4) can be located within the internal cavity (3). The seal member (4) can include a proximal end (41), a distal end (42) and an interior region. The proximal end (41) of the seal member (4) can include a septum (40) having a vertical thickness. The septum (40) can be provided with a slit (43) biased to a closed position. Within the present context and throughout disclosure, the term "vertical" refers to a direction that is on the orientation (+x/−x) along the main axis (A).

The seal member (4) can further include an elastomeric collar (44) located distal from the proximal end (41) of the seal member (4) but closer to the proximal end (41) of the seal member (4) than to the distal end (42) of the seal member (4). A vertical thickness of the collar (44) can be greater than the vertical thickness of the septum (40). Within this context, the term "vertical thickness" corresponds to a respective thickness along the main axis (A).

The seal member (4) can be considered as configured to move between a closed position and a compressed open position when the male luer tip (201) of the medical implement (200) is inserted into the central opening (10) of the proximal body member (1), such that the proximal end (41) of the seal member (4) moves distally in transitioning from the closed position to the open position.

The connector (100) further includes a rigid, hollow elongated portion (5) located within the cavity (3).

The elongated portion (5) includes a body portion (50) and a proximal tip (51) that is more proximal to the first end (11) than the body portion (50). The body portion (50) is tapered, such that a radial width of the body portion (50) decreases towards the proximal tip (51). It can be considered that the body portion (50) extends proximally from the base member (2), and that the proximal tip (51) of the elongated portion (5) is located further in the proximal direction than the proximal end (131) of the abutment surface (13).

The elongated portion (5) can be considered as being surrounded by the seal member (4) around the main axis (A), and located within the seal member (4) when in the closed position. The elongated portion (5) can be considered to include a closed, non-sharp, proximal tip (51) for being received by the male luer tip (201) when in the open position, that is, when the connector (100) is engaged with the implement (200). The tip (51) can include a proximally facing top surface (52) with a transverse width positioned within the interior region of the seal member (4) distally below the septum (40) of the seal member (4) when in the closed position, such that:

- an open space is provided in the interior region of the seal member (4) between the tip (51) of the elongated portion (5) and a distal side of the septum (40),
- the open space is not narrower than the transverse width of the proximally facing top surface (52) of the tip (51) of the elongated portion (5), permitting compression of the seal member (4) to advance unimpeded distally with respect to the elongated portion (5) from the closed position to the open position, to expose the elongated portion (5) proximally outside of the seal member (4).

The elongated portion (5) further includes one or more side openings (53) on the body portion (50); in other words, the one or more side openings (53) are spaced distally from the tip (51). The elongated portion (5) further includes an internal fluid passageway (54) in fluid communication with the one or more side openings (53). Each of the side openings (53) can include a proximal first end (531) and a distal second end (532). In other words, in the one or more side openings (53), the first end (531) is more proximal than the corresponding second end (532) to the central opening (10).

The one or more side openings (53) are more distal than the abutment surface (13). In other words, the first end (531) of at least one of the side openings (53) is located more distal than the distal end (132) of the abutment surface (13). That is, in terms of respective radial projections on the main axis (A), the one or more side openings (53) can be considered as being located in-between the abutment surface (13) and the base member (2).

Contrary to the positioning of the one or more side openings (53) with respect to the abutment surface (13) in the connector (100) according to the disclosure; commercially available neutral displacement medical connectors can be considered as provided with side openings having proximal ends that are more proximal than distal ends of respective abutment surfaces. It can be thus considered that, in the connector (100) according to the disclosure, axial loci of the one or more side openings (53) with regard to the abutment surface (13) are distally shifted when compared to those available commercially. In other words, the first end(s) (531) of the one or more side openings (53) are distally shifted when compared to the commercially available connectors.

On the other hand; considering that the tapered body portion (50) in the connector (100) according to the disclosure radially widens in the distal direction (−x); the fact that the one or more side openings (53) are more distal than the abutment surface (13) allows provision of an increased or enhanced extent of radial fluid flow area at the one or more side openings (53), in comparison with the commercially available connectors discussed above. The reason of this is, in the connector (10) according to the disclosure, the relatively distal locus of the one or more side openings (53) corresponds to a greater circumference around the main axis (A), thereby allowing the one or more side openings (53) to have an enhanced (in other words, greater) width, especially at the second end(s) (532).

Due to the tapered structure of the body portion (50); the amount of body portion (50) building material surrounding the main axis (A) inherently increases in the distal direction (−x). So, thanks to the distally shifted axial loci of the one or more side openings (53); even though the disclosure achieves the above-mentioned enhanced width values at the one or more side openings (53), mechanical resistance of the elongated portion (5) against forces transverse to the main axis (A) is not compromised.

Furthermore, the connector (100) according to the disclosure is easy to produce. Molding can be considered as the economically most feasible way to form the base member (2). At formation of side openings, resulting flow areas would easily deviate from those planned prior to the molding. That is, the flow areas of side openings can be smaller than pre-determined values thereof. The possibility of deviation inherently increases with smaller side openings. The deviation may even result in unacceptably high extent of pressure drop around the side openings at use of the corresponding connectors in communication of medical fluids.

This problem difficilitates the use of the resulting connector (100). In some extreme cases, formation of the side openings (53) may even not be achieved due to the deviation.

Thanks to the improvement explained in the disclosure, greater widths of side openings (53) are rendered available; allowing greater extent of flow areas. Thus, in formation of side openings (53), occurrence of deviations from planned designs are minimized or even eliminated. So, production of the base member (2) of the connector (100) according to the disclosure is easy, and results in one or more side openings (53) that perform as expected. Product return and user complaints are thus minimized or even eliminated. Whether the base member (2) is formed by molding is easy to determine by visual inspection.

Drag forces that difficilitate the fluid communication through side openings (53) decrease with greater ratios of combined flow area to combined lengths of margins that define the geometries of the side openings (53). The enhanced extent of flow areas, thanks to the above-discussed enhanced widths, results in reduction of drag forces during use of the connector (100) according to the disclosure.

The decreased drag forces and minimized extent of pressure difference help for passing medical fluids through the one or more side openings (53) at a desired rate. So, for successfully transferring a medical fluid at a desired ratio, it would be sufficient to manually exert even a relatively small extent of force onto the medical implement (200). Hence, the disclosure provides an easy-to-use and reliable connector.

Thanks to the enhanced mechanical resistance discussed above, the disclosure enables the elongated portion (5) to have sufficient mechanical resistance even with a single side opening (53), without necessitating circumferential distribution of a plurality of side openings (53). The embodiment with a single side opening (53) achieves minimization of the above-mentioned drag, by maximizing the ratio of (combined) flow area to combined lengths of margins that define the geometry of the side opening (53).

The tapered geometry of the body portion (50) allows a generally greater width at relatively distal portions of the one or more side openings (53), than at relatively proximal portions of the side opening(s) (53). That is, the one or more side openings (53) have greater width values at portions that are relatively farther to the first end (531) and relatively closer to the second end (532). For instance, the one or more side openings (53) can have a pyriform (in other words, egg-shaped) geometry, and relatively pointy ends thereof can correspond to respective first ends (531). As another example, the one or more side openings (53) can have a trapezoid (for instance, isosceles trapezoid) geometry having a first base and a second base that is longer when compared to the first base, and the relatively shorter first base can correspond to respective first ends (531).

The enhanced width values available at the one or more side openings (53) in the connector (100) according to the disclosure allow sufficient extent of fluid flow through the one or more side openings (53) even with a decreased extent of axial distance between the first end (531) and second end (532) of the one or more side openings (53), without compromising the above-mentioned mechanical resistance.

Thanks to the fact that the disclosure achieves sufficient side opening (53) flow areas even with a decreased extent of axial distance between the first end (531) and second end (532); at a typical engagement or disengagement of a medical implement (200), axial translational movement of the male luer tip (201) between radial projections of the first end (531) and second end (532) can be completed at a relatively shorter time. In an approach analogous with the latter statement, at a typical engagement or disengagement of a medical implement (200), axial movement of the proximal end (41) (or, slit (43)) of a corresponding seal member (4) between radial projections of the first end (531)

and second end (532) can be completed at a relatively shorter time. This results in minimization of reflux at pulling the male luer tip (201) of the implement (200) in proximal direction (+x) when transiting from the open position to the closed position. Hence, the connector (100) according to the disclosure provides an enhanced reliability. Within the customary meaning in the related field, the term reflux can be also referred to as negative flow.

It can be considered that, in the closed position, the elastomeric collar (44) of the seal member (4) contacts the abutment surface (13) of the body member (1), thereby limiting proximal axial movement of the seal member (4), but not distal axial movement of the seal member (4), such that the proximal end (41) of the seal member (4) is at or near the central opening (10) of the body member (1) in the closed position.

Figure 5:
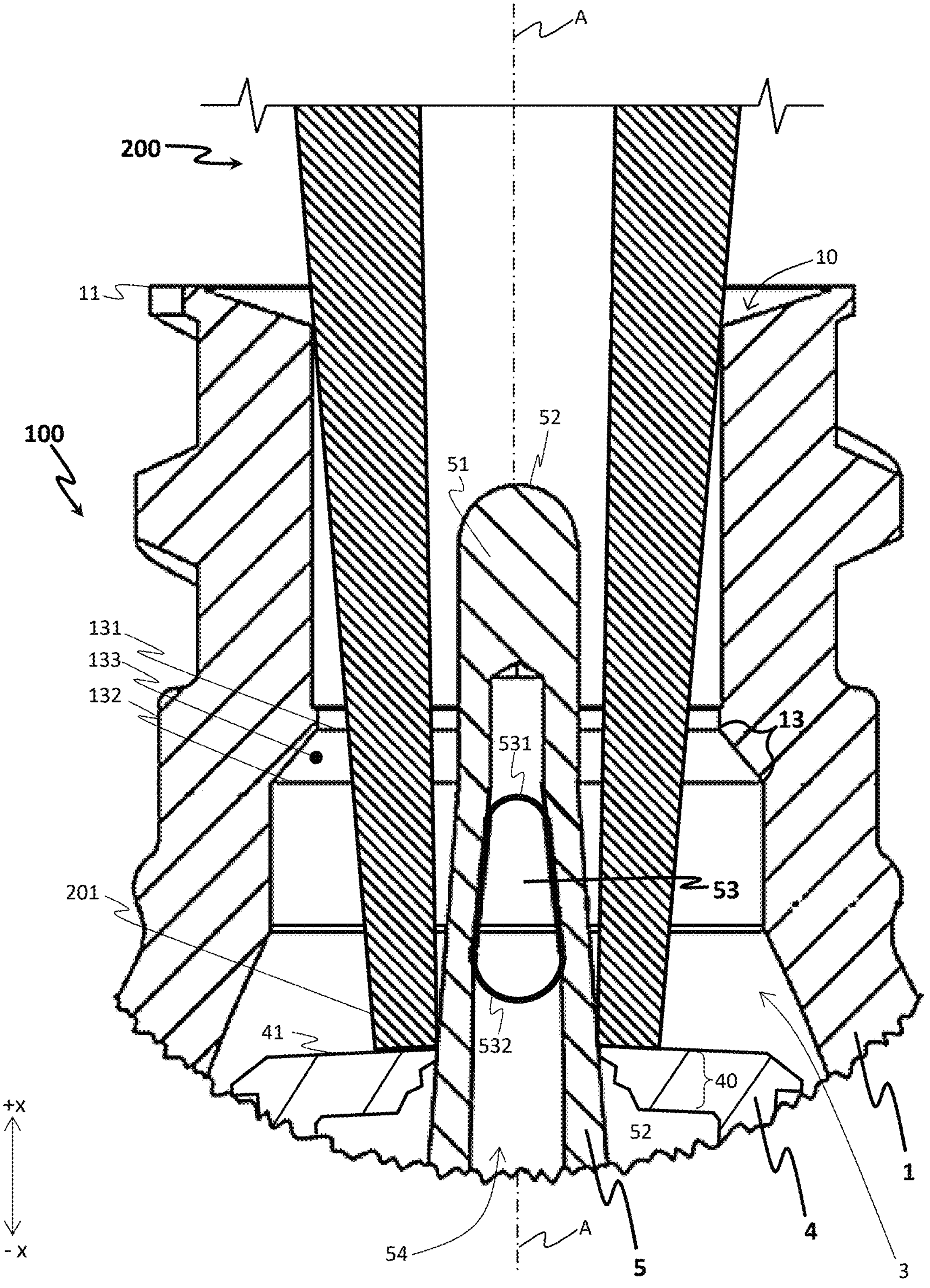
FIG. 5 represents a close-up view of detail J based on FIG. 1 in an open position, showing possible relative positionings between a male luer tip of a medical implement, side opening(s), abutment surface and the first end of the sealing means.

It can be further considered that in the open position, the elastomeric collar (44) is separated from the abutment surface (13) and the central opening (10) of the proximal body member (1). FIG. 5 represents a close-up view of detail J based on FIG. 1 in an open position, showing possible relative positionings between a male luer tip of a medical implement, side opening(s), abutment surface and the first end of the sealing means.

It can be further considered that the one or more side openings (53) of the elongated portion (5) are sized and positioned to permit the male luer tip (201) of the medical implement (200) to be advanced into the proximal body member (1) a sufficient distance to permit the one or more side openings (53) of the elongated portion (5) to be positioned inside of the male luer tip (201) and outside of the interior region of the seal member (4), after the proximal tip (51) of the elongated portion (5) penetrates the proximal end (41) of the seal member (4). These can be arranged such that the proximal end (41) of the seal member (4) is distal from the proximal tip (51) of the elongated portion (5); and fluid in the medical implement (200) is permitted to pass directly from within the male luer tip (201) to the interior of the fluid passageway (54) of the elongated portion (5) without passing through the seal member (4).

In another aspect, or in other words: the disclosure proposes a medical connector (100) defining a main axis (A). The medical connector (100) comprises:

- a body member (1) defining an internal cavity (3) and having a first end (11) and a second end (12) spaced from the first end (11), the first end (11) defining a central opening (10) that communicates with the internal cavity (3), the body member (1) having an internal abutment surface (13);
- a base member (2) coupled to the second end (12) of the body member (1); and
- an elongated portion (5) extending from the base member (2) into the internal cavity (3) of the body member (1) along the main axis (A), the elongated portion (5) defining a passageway (54) and at least one side opening (53).

Within the context of the present disclosure, the elongated portion (5) can be also referred to as elongated member.

The abutment surface (13) is positioned between the central opening (10) and the base member (2), and the at least one side opening (53) is positioned between the abutment surface (13) and the base member (2).

The elongated portion (5) can have a radial width that decreases along the main axis (A) from the base member (2) towards the central opening (10).

The at least one side opening (53) can have a proximal first end (531) and a distal second end (532), the proximal first end (531) positioned closer to the central opening (10) than the distal second end (532).

The distal second end (532) of the at least one side opening (53) can have a greater width than the proximal first end (531) of the at least one side opening (53). Such medical connector can further include a seal member (4) which is positioned about the elongated portion (5) and which includes a septum (40) that defines a slit (43) and is positioned in a way which the septum (40) biases onto the central opening (10), to close the central opening (10) when in a closed position. The septum (40) can be movable from the closed position within the central opening (10) to an open position to expose the at least one side opening (53).

Persons skilled in the art will understand that the structures and methods specifically described herein and illustrated in the accompanying figures are non-limiting exemplary aspects, and that the description, disclosure, and figures should be construed merely as exemplary of particular aspects. It is to be understood, therefore, that this disclosure is not limited to the precise aspects described, and that various other changes and modifications may be effectuated by one skilled in the art without departing from the scope or spirit of the disclosure. Additionally, it is envisioned that the elements and features illustrated or described in connection with one exemplary aspect may be combined with the elements and features of another without departing from the scope of this disclosure, and that such modifications and variations are also intended to be included within the scope of this disclosure. Indeed, any combination of any of the disclosed elements and features is within the scope of this disclosure. Accordingly, the subject matter of this disclosure is not to be limited by what has been particularly shown and described.

The invention claimed is:

1. A medical connector defining a main axis, the medical connector comprising:

- a body member having a first end and a second end distal to the first end, a base member that is coupled to the body member, and an internal cavity formed between the body member and the base member, the first end of the body member defining a central opening for receiving a male luer tip of a medical implement to deliver fluid through the central opening;
- the body member further including an internal abutment surface located in-between the central opening and the second end of the body member along the main axis, the abutment surface having a proximal end, a distal end, and a slanting wall extending between the proximal end and the distal end such that the proximal end of the abutment surface is narrower than the distal end of the abutment surface; and
- a rigid, hollow elongated portion located within the cavity;
- wherein the elongated portion includes a body portion and a proximal tip that is more proximal to the first end than the body portion,
- the body portion being tapered, such that a radial width of the body portion decreases towards the proximal tip;
- the elongated portion defining one or more side openings on the body portion, and including an internal fluid passageway in fluid communication with the one or more side openings, the one or more side openings having a first end and a second end, the first end of the one or more side openings being relatively closer to the central opening when compared to the second end of the one or more side openings, the first end of the one or more side openings positioned distally of the distal end of the abutment surface, wherein the body portion extends proximally from the base member, and the proximal tip of the elongated portion is located proximally of the proximal end of the abutment surface.

2. The medical connector according to claim 1, wherein the one or more side openings have a trapezoid geometry having a first base and a second base that is longer when compared to the first base.

3. The medical connector according to claim 2, wherein the first base corresponds to the first end of the respective one of the side openings.

4. The medical connector according to claim 2, wherein said trapezoid geometry is an isosceles trapezoid geometry.

5. The medical connector according to claim 1, wherein the one or more side openings includes a single side opening.

6. The medical connector according to claim 1, further including an elastomeric seal member located within the internal cavity of the body member, the seal member having a proximal end, a distal end, and an interior region, the proximal end of the seal member including a septum having a vertical thickness and defining a slit biased to a closed position.

7. The medical connector according to claim 6, wherein the seal member further includes an elastomeric collar located distal from the proximal end of the seal member but closer to the proximal end of the seal member than to the distal end of the seal member.

8. The medical connector according to claim 7, wherein a vertical thickness of the collar is greater than the vertical thickness of the septum.

9. The medical connector according to claim 6, wherein the seal member is configured to move between the closed position and an open position in which the seal member is compressed when the male luer tip of the medical implement is inserted into the central opening.

10. The medical connector according to claim 1, wherein the proximal tip of the elongated portion is closed and non-sharp for being received by the male luer tip when the seal member is in the open position.

11. The medical connector according to claim 1, wherein the base member is formed by molding.

12. The medical connector according to claim 1, wherein the base member includes a male luer end.

13. A medical connector defining a main axis, the medical connector comprising:

a body member having a first end and a second end distal to the first end, a base member that is coupled to the body member, and an internal cavity formed between the body member and the base member, the first end of the body member defining a central opening for receiving a male luer tip of a medical implement to deliver fluid through the central opening;

the body member further including an internal abutment surface located in-between the central opening and the second end of the body member along the main axis, the abutment surface having a proximal end, a distal end, and a slanting wall extending between the proximal end and the distal end such that the proximal end of the abutment surface is narrower than the distal end of the abutment surface; and a rigid, hollow elongated portion located within the cavity;

wherein the elongated portion includes a body portion and a proximal tip that is more proximal to the first end than the body portion, the body portion being tapered, such that a radial width of the body portion decreases towards the proximal tip;

the elongated portion defining one or more side openings on the body portion, and including an internal fluid passageway in fluid communication with the one or more side openings, the one or more side openings having a first end and a second end, the first end of the one or more side openings being relatively closer to the central opening when compared to the second end of the one or more side openings, the first end of the one or more side openings positioned distally of the distal end of the abutment surface, wherein the one or more side openings have a pyriform geometry, the first end of the one or more side openings being more pointy when compared to the second end of the one or more side openings.

14. The medical connector according to claim 13, wherein the first end of the one or more side openings has the pyriform geometry.

15. A medical connector defining a main axis, the medical connector comprising:

a body member defining an internal cavity and having a first end and a second end spaced from the first end, the first end defining a central opening that communicates with the internal cavity, the body member having an internal abutment surface including a proximal end and a distal end;

a base member coupled to the second end of the body member; and an elongated portion extending from the base member into the internal cavity of the body member along the main axis, the elongated portion defining a passageway and at least one side opening;

wherein the internal abutment surface is positioned between the central opening and the base member, and the at least one side opening is positioned in its entirety between the distal end of the abutment surface and the base member, wherein the elongated portion has a radial width that decreases along the main axis from the base member towards the central opening, and the at least one side opening has a proximal first end and a distal second end, the proximal first end positioned closer to the central opening than the distal second end, and wherein the distal second end of the at least one side opening has a greater width than the proximal first end of the at least one side opening.

16. The medical connector of claim 15, further including a seal member, the seal member positioned about the elongated portion and including a septum that defines a slit and is positioned, such that the septum is movable from a closed position within the central opening to an open position to expose the at least one side opening.

* * * * *